(12) United States Patent  
Botten

(10) Patent No.: US 12,220,342 B2
(45) Date of Patent: Feb. 11, 2025

(54) OSTOMY POUCH CLOSURE SYSTEM

(71) Applicant: HOLLISTER INCORPORATED, Libertyville, IL (US)

(72) Inventor: Ronald S. Botten, Libertyville, IL (US)

(73) Assignee: HOLLISTER INCORPORATED, Libertyville, IL (US)

( * ) Notice: Subject to any disclaimer, the term of this patent is extended or adjusted under 35 U.S.C. 154(b) by 0 days.

(21) Appl. No.: 18/705,324

(22) PCT Filed: Dec. 22, 2022

(86) PCT No.: PCT/US2022/053767
§ 371 (c)(1),
(2) Date: Apr. 26, 2024

(87) PCT Pub. No.: WO2023/129463
PCT Pub. Date: Jul. 6, 2023

(65) Prior Publication Data
US 2024/0325188 A1    Oct. 3, 2024

Related U.S. Application Data

(60) Provisional application No. 63/294,411, filed on Dec. 29, 2021.

(51) Int. Cl.
*A61F 5/44* (2006.01)
*A61F 5/449* (2006.01)

(52) U.S. Cl.
CPC ............ *A61F 5/4407* (2013.01); *A61F 5/449* (2013.01)

(58) Field of Classification Search
CPC .............................. A61F 5/4407; A61F 5/449
See application file for complete search history.

(56) References Cited

U.S. PATENT DOCUMENTS 3,825,005 A * 7/1974 Fenton ................. A61F 5/4407
604/335
5,968,024 A * 10/1999 Freeman ............... A61F 5/4407
604/323

(Continued)

FOREIGN PATENT DOCUMENTS

WO    2020/226861 A1    11/2020

OTHER PUBLICATIONS

International Search Report and Written Opinion for International Patent Application No. PCT/US2022/053767, dated Mar. 2, 2023, 8 pages.

*Primary Examiner* — Susan S Su
*Assistant Examiner* — Erin A Kim
(74) *Attorney, Agent, or Firm* — Klintworth & Rozenblat IP LLP

(57) ABSTRACT

A closure system for a drainable ostomy appliance, which appliance includes a body side wall and a non-body side wall sealed to one another to define a collection cavity and a neck portion terminating in a discharge outlet. The closure system includes a first portion on the body side wall having first and second closure members defining a gap therebetween and a second portion on the non-body side wall having third and fourth closure members. In an open state, the neck portion is unfolded. In a closed state, the first closure member is folded onto the third closure member at a loose fold and the first, second and third closure members are folded onto the fourth closure member with the first closure member proximal the fourth closure member at a tight fold to form a seal between the third closure member and the fourth closure member.

15 Claims, 2 Drawing Sheets

(56) References Cited

U.S. PATENT DOCUMENTS

| | | | |
|---|---|---|---|
| 6,419,664 B1* | 7/2002 | von Bulow | A61F 5/4407 604/327 |
| 2004/0049837 A1* | 3/2004 | Falconer | A61F 5/4407 383/88 |
| 2005/0159717 A1 | 7/2005 | Holtermann | |
| 2008/0033379 A1 | 2/2008 | Pedersen | |
| 2013/0253456 A1* | 9/2013 | Friske | A61F 5/4407 604/332 |
| 2019/0328572 A1* | 10/2019 | Weinberg | A61F 5/4407 |
| 2021/0100679 A1* | 4/2021 | Hoggarth | A61F 5/4404 |

* cited by examiner

OSTOMY POUCH CLOSURE SYSTEM

BACKGROUND

The following description relates generally to an ostomy pouch closure system and more particularly to a drainable ostomy pouch closure system.

Ostomy pouches for collecting body waste are used by patients who have had surgery such as a colostomy, ileostomy, or urostomy. Ostomy pouches typically include flat, opposing side walls secured to one another along their peripheral edges to define a collection cavity. An opening for receiving a stoma is formed in one of the side walls, and includes a securing means or system, such as an adhesive barrier, to secure the pouch to the user so that body waste discharged through the stoma is received within the cavity.

Some ostomy pouches may be closed-end pouches designed for single use, in which the entirety of the peripheral edges are sealed to one another and the pouch is discarded after it has been substantially filled with stomal discharge. Other ostomy pouches are drainable pouches that include a discharge opening at a lower end that can be closed during collection of body waste material but may be opened for draining body waste material from the pouch after a period of use. Such drainable pouches are disclosed, for example, in Nolan, U.S. Pat. No. 3,523,534, and Jensen et al., U.S. Pat. No. 4,411,659, which are incorporated herein in their entirety by reference.

The discharge opening of drainable pouches is typically formed at the end of a narrowed neck portion. The end of the neck portion has closure means (or a closure system) for maintaining the discharge opening in a sealed state until waste material is to be drained from the pouch. Some closure systems include a clamp, as in the aforementioned Nolan patent, or a device such as a conventional wire tie or wrap for securing the neck portion in an upwardly-rolled condition.

Drainable pouches should be easy to drain without the risk of soiling one's clothes or the surroundings. Pouches should also be easy to close securely after being drained and amenable to being cleaned after drainage and before re-closing, so that the risk of an unpleasant odor is substantially reduced. Most importantly, the closure system should provide a secure seal when closed to minimize the risk of leakage.

A number of different closure system solutions that facilitate closing, cleaning and drainage operations are known. For example, systems that include upwardly folding portions of the neck with a number of integral spring-like biasing members include Villefrance et al., U.S. Pat. No. 7,879,015 and Friske et al., U.S. Pat. No. 8,672,907, which are commonly assigned with the present application and incorporated herein in their entirety by reference.

Other drainable pouches having integral closure systems include Friske et al., U.S. Pat. No. 9,011,395, which includes four closure members and a two-part fastening system, in which one closure member is provided on a body-side pouch outlet and three closure members are provided on a distal-side pouch outlet, which patent is commonly assigned with the present application and incorporated herein in its entirety by reference.

While all of these system function well, there are critical tolerances for positioning of the stiffening ribs that must be met in order for the closure systems to function properly.

Accordingly, it is desirable to provide an ostomy appliance, such as an ostomy pouch, with a closure system that uses stiffening ribs to effect proper closure. Desirably, such a system provides secure closure with less reliance on the positioning of the stiffening ribs relative to one another on the pouch films.

SUMMARY

According to one embodiment, a drainable ostomy appliance includes side walls of flexible sheet material sealed to one another along a portion of their respective peripheries to define a collection cavity. The side walls are a body side wall and a non-body side wall. An inlet is formed in the body side wall.

The side walls define a downwardly extending neck portion terminating in a discharge outlet at which the side walls are not sealed to one another. The discharge outlet is closed by folding the neck portion upwardly and opened by unfolding the neck portion downwardly for draining the contents from the cavity.

The closure system includes a first portion and a second portion. The first portion is on the body side wall and the second portion is on the non-body side wall. The first portion includes a first closure member and a second closure member. The first closure member is proximal the discharge outlet and the second closure member is distal of the discharge outlet. The first and second closure members define a gap therebetween. The second portion of the closure system is on the non-body side wall and includes a third closure member and a fourth closure member.

In an open state, the neck portion is unfolded. In a closed state, the first closure member is folded onto the third closure member at a loose fold and the first, second and third closure members are folded onto the fourth closure member with the first closure member proximal the fourth closure member at a tight fold to form a seal between the third closure member and the fourth closure member. The neck portion may be secured in the closed state using a fastening system.

In embodiments, the first, second, third and fourth closure members are formed from a stiff, flexible, spring-like material. The material can be a polymeric material. Suitable polymeric materials include polyethylene (PE) and ethylene vinyl acetate (EVA).

In embodiments, the first, second, third and fourth closure members have preferential fold lines formed therein. In an embodiment, the preferential fold lines are slits or pre-defined grooves formed into a portion of the first, second, third and fourth closure members. In the open state, the preferential fold lines in the first and second closure members are aligned, the preferential fold lines in the second and third closure members are aligned, and the preferential fold lines in the third and fourth closure members are aligned. In embodiments, the preferential fold lines are predefined grooves in the closure members.

In embodiments, the first and third closure members partially overlie one another on opposing sides of the discharge outlet.

In embodiments, the first and second closure members are mounted to the body side wall such that a portion of each of the first and second closure members is adhered to the body side wall and another portion of each of the first and second closure members is not adhered to the body side wall. The third and fourth closure members can be mounted to the non-body side wall such that a portion of each of the third and fourth closure members is adhered to the non-body side wall and another portion of each of the third and fourth closure members is not adhered to the non-body side wall.

The portion of each of the first and second closure members not adhered to the body side wall are proximal one another and the portion of each of the third and fourth closure members not adhered to the non-body side wall are proximal one another.

Other objects, features, and advantages of the disclosure will be apparent from the following description, taken in conjunction with the accompanying sheets of drawings, wherein like numerals refer to like parts, elements, components, steps, and processes.

BRIEF DESCRIPTION OF THE DRAWINGS

FIGS. 4A-4C are sectional views of the pouch illustrating the folding of the closure system, in which FIG. 4A illustrates the pouch in an open or unfolded state, FIG. 4B illustrates a first fold of the closure system, and FIG. 4C illustrates a second fold of the closure system to a closed state;

DETAILED DESCRIPTION

Figure 1:
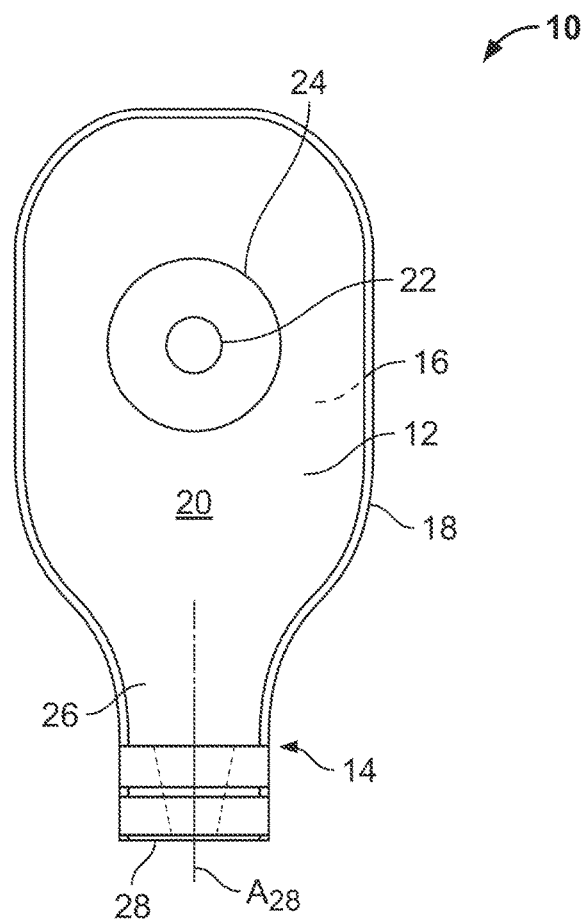
FIG. 1 is a body side view of an ostomy pouch having an embodiment of a closure system in accordance with the present disclosure.

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

FIG. 1 illustrates a drainable ostomy appliance or pouch 10, showing the body facing side 12 and shows an ostomy pouch closure system 14, according to an embodiment. The drainable pouch includes an outer wall (or non-body side wall) 16 and the body side wall 12, which are joined along their peripheral edges 18 to define a collection cavity 20 for collecting stomal discharge. The pouch 10 includes an opening 22 for receiving a stoma and a member 24 for securing the pouch 10 to a user, which member 24 surrounds the opening 22. The securing member 24 can be, for example, a one-piece barrier or a two-piece barrier that includes mating coupling rings (not shown). The one- and two-piece barriers will be appreciated by those skilled in the art.

The drainable pouch 10 also has a downwardly extending neck portion 26 terminating in a discharge opening or outlet 28 for draining the contents collected in the cavity 20 after a period of use. The discharge outlet 28 is closed during use by folding the neck portion 26 upwardly and securing it in the upwardly folded position.

The side walls 12, 16 are formed of a suitable flexible sheet material, such as a polymeric film, which can be a monolayer or multilayer film. Each of the walls 12, 16 can be formed of one continuous flexible film to define the entire pouch 10 including the neck portion 26. Alternatively, the walls 12, 16 of the neck portion 26 can be formed of separate flexible films than the walls 12, 16 of the pouch 10 body. That is, the walls of the neck portion 26 may be formed of a different polymeric film than the walls of the pouch body.

Figures 2, 3:
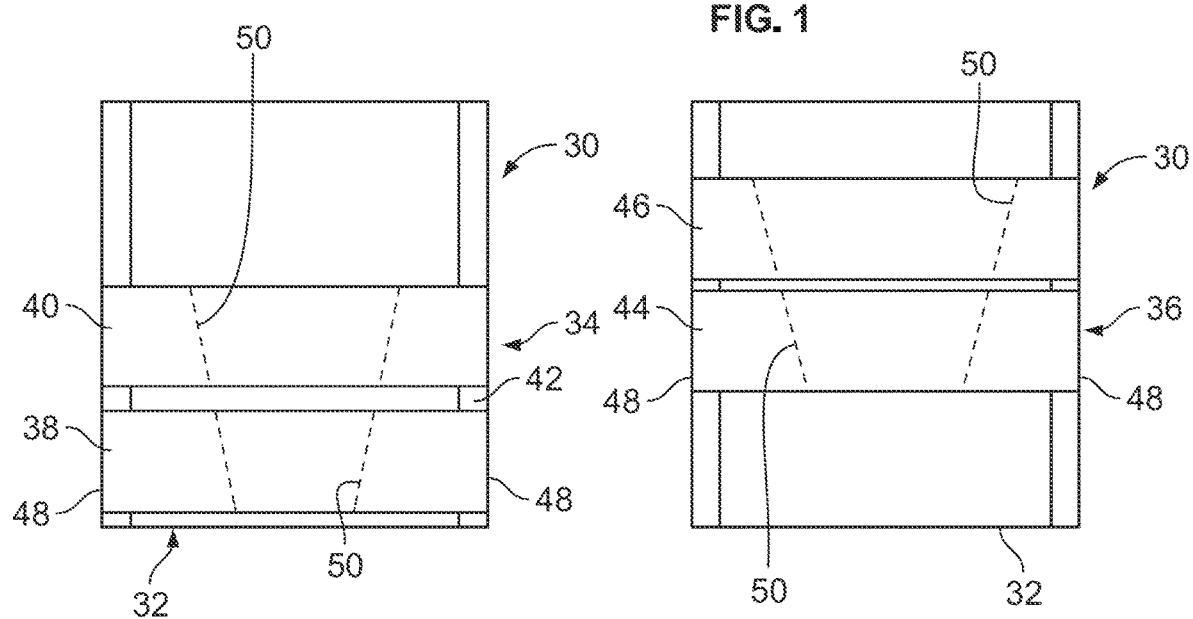
FIG. 2 is a body side view of the lower portion of the pouch illustrating portions of the closure system, according to an embodiment.
FIG. 3 is a non-body side view of a lower portion of the pouch illustrating portions of the closure system, according to an embodiment.

Referring now FIG. 2 there is shown a body side view of a lower portion 30 of the pouch 10. The peripheral edges 18 of the walls 12, 16 are sealed along their respective sides but are not sealed at the bottom, as indicated at 32, which non-sealed region defines the discharge outlet 28 through which stomal discharge can be emptied from the pouch 10.

The closure system 14 includes a first portion 34 on the body side wall 12 and (as shown in FIG. 3) a second portion 36 on the non-body side wall 16. First and second body side closure members 38, 40 are positioned on the body side wall 12 with the body side wall first closure member 38 proximal to the discharge outlet 28 and the second closure member 40 distal from the discharge outlet 28. The first and second body side closure members 38, 40 are spaced from one another to define a gap 42 therebetween. The first and second body side closure members 38, 40 may be configured to provide a structure (more than flimsy film) such that a user can hold and control the pouch neck portion 26 for opening of the discharge outlet 28. In some embodiments, the first portion 34 may only include one body side closure member 38. In an embodiment, the second body side closure member 40 may be sized to fit inside the periphery seal 18 to allow the pouch neck portion 26 to open completely without creating tight corners.

Referring to FIG. 3, there is shown a non-body side wall 16 view of the lower portion 30 of the pouch 10. Like the body side wall 12, the non-body side wall 16 includes closure members, referred to as third 44 and fourth 46 closure members, with the non-body side third closure member 44 proximal to the discharge outlet 28 and the fourth closure member 46 distal from the discharge outlet 28. In an embodiment, the third and fourth (non-body side) closure members 44, 46 abut one another.

In an embodiment, the closure members 38, 40, 44, 46 are formed from a stiff but flexible, spring-like polymeric material. The members 38, 40, 44, 46 are normally flat and disposed in straight parallel relation to each other. The material is somewhat rigid but can be bent or flexed to open the discharge opening 28. That is, when in a relaxed state, the closure members 38, 40, 44, 46 maintain the opening 28 in a relatively closed state. But, when the ends 48 of the members 38, 40, 44, 46 are squeezed together (squeezed toward a centerline $A_{28}$ of the discharge opening 28), the members 38, 40, 44, 46 flex or bow outward so as to open the discharge opening 28. Suitable materials for the closure members 38, 40, 44, 46 include polyethylene (PE), ethylene vinyl acetate (EVA) and the like.

To facilitate the flexing or bowing outward, in embodiments, the closure members 38, 40, 44, 46 can include preferential fold lines 50 in the members 38, 40, 44, 46. The preferential fold lines 50 can be formed as predefined grooves or partial slits in the members 38, 40, 44, 46; the grooves or slits 50 are partial in that they do not extend fully through the member 38, 40, 44, 46. In embodiments, the preferential fold lines 50 can be formed as predefined grooves formed in the members 38, 40, 44, 46. As seen in FIGS. 2 and 3, the fold lines 50 in the body side members 38, 40 are closer to one another than the fold lines 50 in the non-body side members 44, 46 and the fold lines in the first and third members 38, 44 are closer to one another than the fold lines 50 in the second and fourth members 40, 46. In an embodiment in which the second member 40 overlies a portion of the third member 44, the fold lines 50 in the second member 40 and the fold lines 50 in the third member 44 may likewise overlie one another. In this manner, when the ends 48 of the members 38, 40, 44, 46 are squeezed toward one another to open the discharge opening 28, the folds lines 50 generally all align with one another to form a funnel-like discharge for the pouch 10.

Figure 4A:
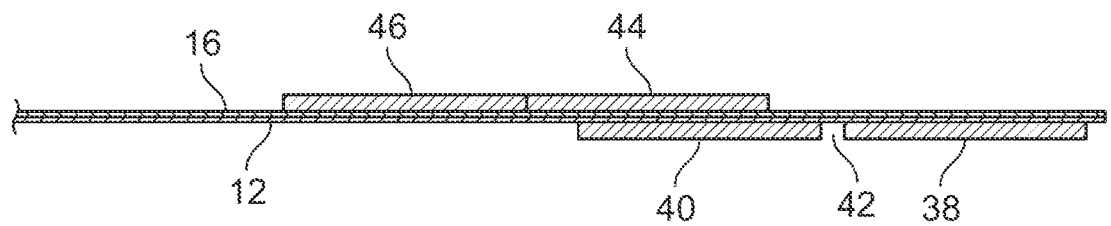
Figure 4B:
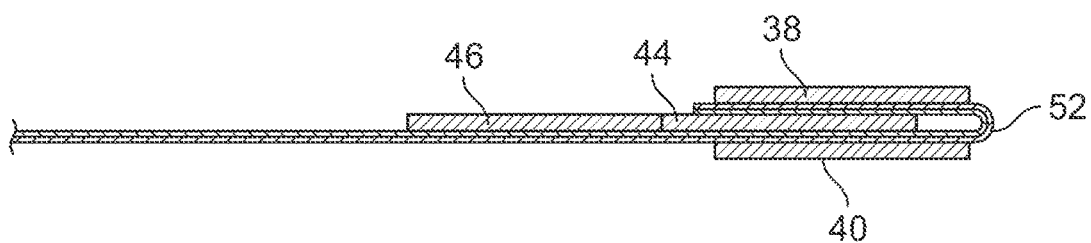
Figure 4C:
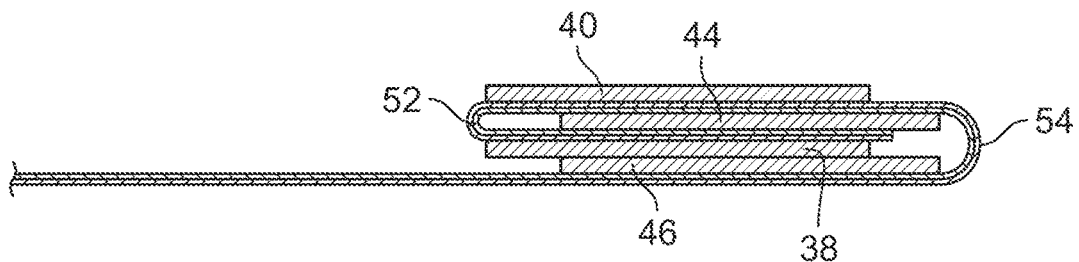

Referring now to FIGS. 4A-4C, the folding of the pouch neck portion 26 to close the discharge opening 28 will be discussed. FIG. 4A shows the pouch 10 with the pouch neck portion 26 unfolded. As noted above, the body side closure members 38, 40 are spaced from one another by the gap 42. The non-body side closure members 44, 46 may be in abutting relationship.

Referring to FIG. 4B, as the first fold (indicated at 52) is made, the first closure member 38 is folded onto the third closure member 44. The space or gap 42 between the first and second members 38, 40 allows for a loose fold that is dependent upon the size of the gap 42 between the members 38, 40.

Referring now to FIG. 4C, as the second fold (indicated at 54) is made, the first and second members 38, 40 and the third member 44 are folded onto the fourth member 46. The tight fold and stretch of the pouch material at the fold 54 between the third and fourth members 44, 46 establishes the pouch 10 seal. The relationship between the thickness of the members, for example members 40, 44 and the size of the gap, for example gap 42 creates the necessary tension to establish the closure seal, without high placement tolerances of the members 38, 40, 44, 46.

Figure 5:
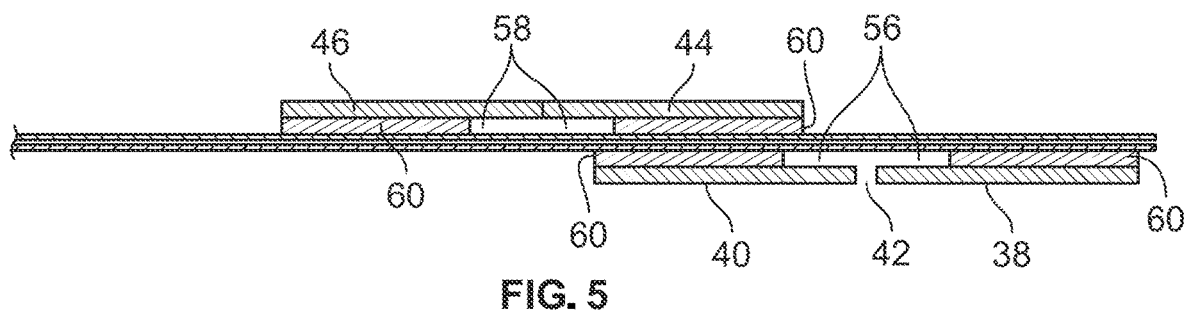
FIG. 5 is a sectional view of the of the pouch illustrating an embodiment of the closure system and showing the anchor points of the stiffening members to the pouch films.

In embodiments, the closure members 38, 40, 44, 46 are adhered, for example, by an adhesive 60, heat sealing or the like, to the pouch 10. In embodiments, the members 38, 40, 44, 46 need not be fully adhered to the pouch 10. As seen in FIG. 5, in the direction of the length of the pouch, that is in the direction along the centerline $A_{28}$ of the outlet 28, the entirety of the closure members 38, 40, 44, 46 need not be fully adhered to the pouch 10. Portions, as indicated at 56 of the first and second members 38, 40 nearer to one another can be unadhered to the pouch 10, or the members 38, 40 can be fully adhered to the pouch 10. Portions, as indicated at 58, of the third and fourth members 44, 46 nearer to one another can be unadhered to the pouch 10. This will allow for elastic deformation, e.g., stretching, of the pouch 10 films between the third and fourth members 44, 46 (as at fold line 54) when folding (as seen in FIG. 4C).

It will be appreciated that unlike known closure systems, the present closure system 14 is less if at all dependent upon locational tolerances between the first and second (body side) 38, 40 and the third and fourth (non-body side) 44, 46 closure members. That is, the alignment of the body side closure members 38, 40 and the non-body side closure members 44, 46 is not critical as with prior known closure systems. Because the present closure system 14 uses a loose fold, as at 52, between the first and second (body side) members 38, 40 and a tight fold, as at 54, between the third and fourth (non-body side) members 44, 46, the location of the first and second 38, 40 members relative to the third and fourth 44, 46 members is not dependent on an exact location and does not require exacting or tight tolerances, and as such, alignment of the first and second members 38, 40 with respect to the third and fourth members 44, 46 is not critical.

Figure 6:
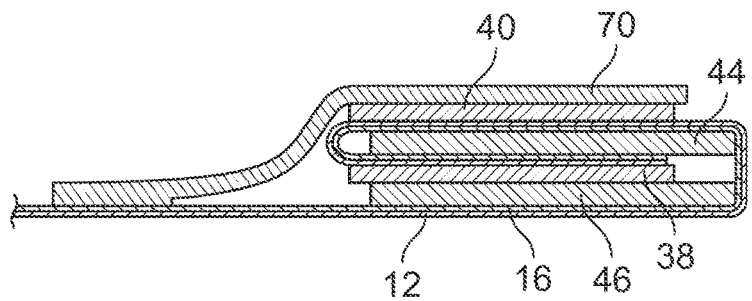
FIG. 6 is a sectional view of the pouch in the closed state of FIG. 4C secured via a two-part fastening system according to an embodiment.

It will be appreciated, although not shown in FIGS. 1-5 as it is well known in the art, the ostomy pouch closure system 14 also includes a fastening system for securing the pouch neck portion 26 in a folded up and closed position, for example, after the second fold as shown in FIG. 4C. In some embodiments, the ostomy pouch closure system 14 may include a two-part fastening system comprising first and second fastener strips, such as hook and loop fasteners. In an embodiment, the closure system 14 may include a flap 70 attached to the non-body side wall 16 adjacent the fourth closure member 46, wherein the flap includes a first fastener strip and the second closure member 40 includes a second fastener strip configured to engage with the first fastener strip to secure the folded neck portion in a closed position as shown in FIG. 6. Alternatively, the second closure member 40 may be replaced with a second fastener strip. In another embodiment, the second fastener strip may be attached to the body side wall 12 adjacent the second closure member 40, wherein the pouch neck portion 26 may be configured to be folded three times (a third fold after the second fold shown in FIG. 4C) and secured in a closed position by engaging the first fastener strip provided on the flap 70 with the second fastener strip.

All patents referred to herein, are hereby incorporated herein in their entirety, by reference, whether or not specifically indicated as such within the text of this disclosure. In the present disclosure, the words "a" or "an" are to be taken to include both the singular and the plural. Conversely, any reference to plural items shall, where appropriate, include the singular. In additions, various features described with respect to any of the embodiments above may be used together, implemented in, or replace features in any of the other embodiments described above.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

The invention claimed is:

1. A drainable ostomy appliance, comprising:
    side walls of flexible sheet material sealed to one another along a portion of their respective peripheries to define a collection cavity, the side walls being a body side wall and a non-body side wall, the side walls defining a downwardly extending neck portion terminating in a discharge outlet at which the side walls are not sealed to one another, the discharge outlet being closed by folding the neck portion upwardly and opened by unfolding the neck portion downwardly for draining the contents from the cavity;
    an inlet in the body side wall; and
    a closure system, comprising:
        a first portion of the closure system positioned on the body side wall, the first portion of the closure system including a first closure member and a second closure member, the first closure member being proximal the discharge outlet and the second closure member being distal of the discharge outlet, the first and second closure members defining a gap therebetween, and wherein the first closure member and the second closure member are both attached to the body side wall;
        a second portion of the closure system positioned on the non-body side wall, the second portion of the closure system including a third closure member and a fourth closure member, wherein the third closure member and the fourth closure member are both attached to the non-body side wall; and a fastening system, wherein in an open state, the neck portion is unfolded and in a closed state, the first closure member is folded onto the third closure member at a first fold and the first, second and third closure members are folded onto the fourth closure member with the first closure member proximal the fourth closure member at a second fold to form a seal between the third closure member and the fourth closure member, wherein the second fold is tighter than the first fold, and wherein the neck portion is secured in the closed state using the fastening system.

2. The ostomy appliance of claim 1, wherein the first, second, third, and fourth closure members are formed from a stiff, flexible, spring-like material.

3. The ostomy appliance of claim 2, wherein the material is a polymeric material.

4. The ostomy appliance of claim 3, wherein the polymeric material is polyethylene (PE) or ethylene vinyl acetate (EVA).

5. The ostomy appliance of claim 1, wherein the first, second, third, and fourth closure members have preferential fold lines formed therein.

6. The ostomy appliance of claim 5, wherein the preferential fold lines are predefined grooves formed into a portion of the first, second, third, and fourth closure members.

7. The ostomy appliance of claim 5, wherein the preferential fold lines are slits formed into a portion of the first, second, third and fourth closure members.

8. The ostomy appliance of claim 5, wherein when in the open state, the preferential fold lines in the first and second closure members are aligned, the preferential fold lines in the second and third closure members are aligned, and the preferential fold lines in the third and fourth closure members are aligned.

9. The ostomy appliance of claim 1, wherein the first and third closure members partially overlie one another on opposing sides of the discharge outlet.

10. The ostomy appliance of claim 1, wherein the first and second closure members are mounted to the body side wall such that a portion of each of the first and second closure members is adhered to the body side wall and another portion of each of the first and second closure members is not adhered to the body side wall.

11. The ostomy appliance of claim 1, wherein the third and fourth closure members are mounted to the non-body side wall such that a portion of each of the third and fourth closure members is adhered to the non-body side wall and another portion of each of the third and fourth closure members is not adhered to the non-body side wall.

12. The ostomy appliance of claim 10, wherein the third and fourth closure members are mounted to the non-body side wall such that a portion of each of the third and fourth closure members is adhered to the non-body side wall and another portion of each of the third and fourth closure members is not adhered to the non-body side wall.

13. The ostomy appliance of claim 10, wherein the portion of each of the first and second closure members not adhered to the body side wall are proximal one another.

14. The ostomy appliance of claim 11, wherein the portion of each of the third and fourth closure members not adhered to the non-body side wall are proximal one another.

15. The ostomy appliance of claim 1, further including a two-piece coupling for securing to a user's body.

* * * * *